(12) United States Patent
Shin

(10) Patent No.: US 11,154,506 B2
(45) Date of Patent: Oct. 26, 2021

(54) METHOD OF MANUFACTURING SPHEROID HAVING UNIFORM SIZE

(71) Applicant: Pensees Inc., Seoul (KR)

(72) Inventor: Jaeha Shin, Seoul (KR)

(73) Assignee: Pensees Inc., Seoul (KR)

( * ) Notice: Subject to any disclaimer, the term of this patent is extended or adjusted under 35 U.S.C. 154(b) by 0 days.

(21) Appl. No.: 16/864,303

(22) Filed: May 1, 2020

(65) Prior Publication Data

US 2021/0186881 A1    Jun. 24, 2021

(30) Foreign Application Priority Data

Dec. 24, 2019 (KR) .......................... 10-2019-0174204

(51) Int. Cl.
| | | |
|---|---|---|
| *A61K 9/16* | (2006.01) | |
| *A61K 9/06* | (2006.01) | |
| *A61K 47/69* | (2017.01) | |

(52) U.S. Cl.
CPC .............. *A61K 9/1658* (2013.01); *A61K 9/06* (2013.01); *A61K 9/1652* (2013.01); *A61K 47/6903* (2017.08)

(58) Field of Classification Search
CPC ...... A61K 9/16; A61K 47/42; C12N 2500/50; C12N 2513/00
See application file for complete search history.

(56) References Cited

U.S. PATENT DOCUMENTS

2009/0163607 A1 * 6/2009 Mine .................... B01J 13/0052
516/98

FOREIGN PATENT DOCUMENTS

| CN | 101330970 A | * | 12/2008 | .......... B01J 13/0052 |
| KR | 10-2018-0117179 A | | 10/2018 | |
| WO | WO-2017149296 A1 | * | 9/2017 | ............ C12M 25/14 |

OTHER PUBLICATIONS

Alruwaili et al (BioDesign and Manufacturing, Jul. 2019, pp. 1-9) (Year: 2019).*
Orban et al (Wiley Periodicals, 2004, pp. 756-762) (Year: 2004).*
Stuart K. Williams et al., "Encapsulation of Adipose Stromal Vascular Fraction Cells in Alginate Hydrogel Spheroids Using a Direct-Write Three-Dimensional Printing System", BioResearch Open Access, Dec. 2013, pp. 448-454, vol. 2, No. 6.
Laurine Valot et al., "Chemical insights into bioinks for 3D printing", Chem. Soc. Rev., Aug. 7, 2019, pp. 4049-4086, vol. 48, No. 15.

* cited by examiner

*Primary Examiner* — Mark V Stevens
(74) *Attorney, Agent, or Firm* — Knobbe, Martens, Olson & Bear, LLP

(57) ABSTRACT

The present invention relates to a method of manufacturing a spheroid using a composition for a liquid bath for dipping a hydrogel droplet and to a spheroid manufactured thereby. The method of manufacturing the spheroid according to the present invention is capable of successfully forming a spheroid having a 3D spherical shape that is difficult to implement on a planar substrate and also of realizing a spheroid having a uniform size, and thus can be effectively used as a technique for obtaining a spheroid having a 3D spherical shape and a uniform size in the field of cell culture.

8 Claims, 12 Drawing Sheets

[Figure 1]
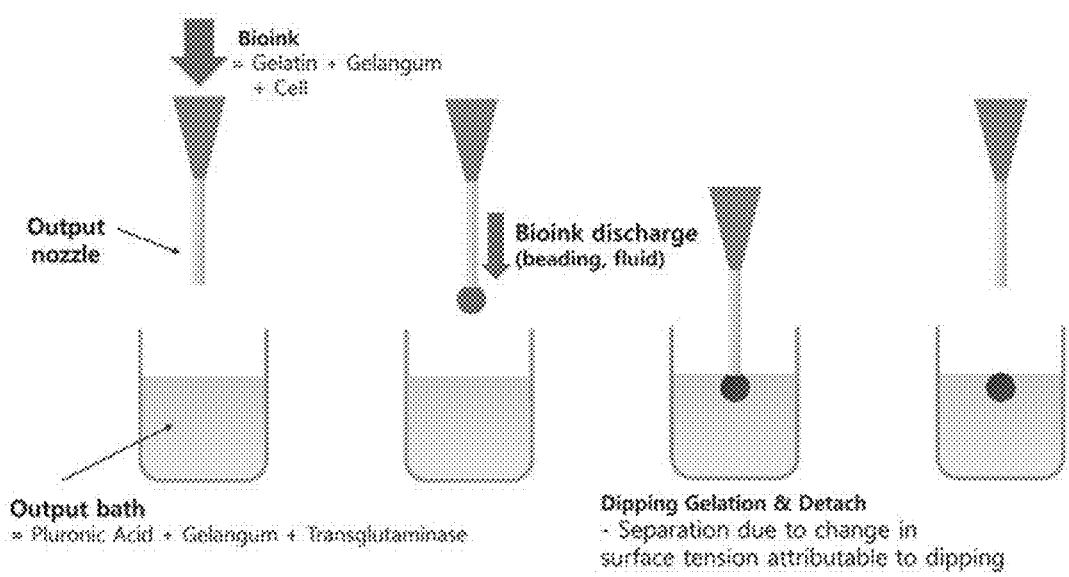

[Figure 2]
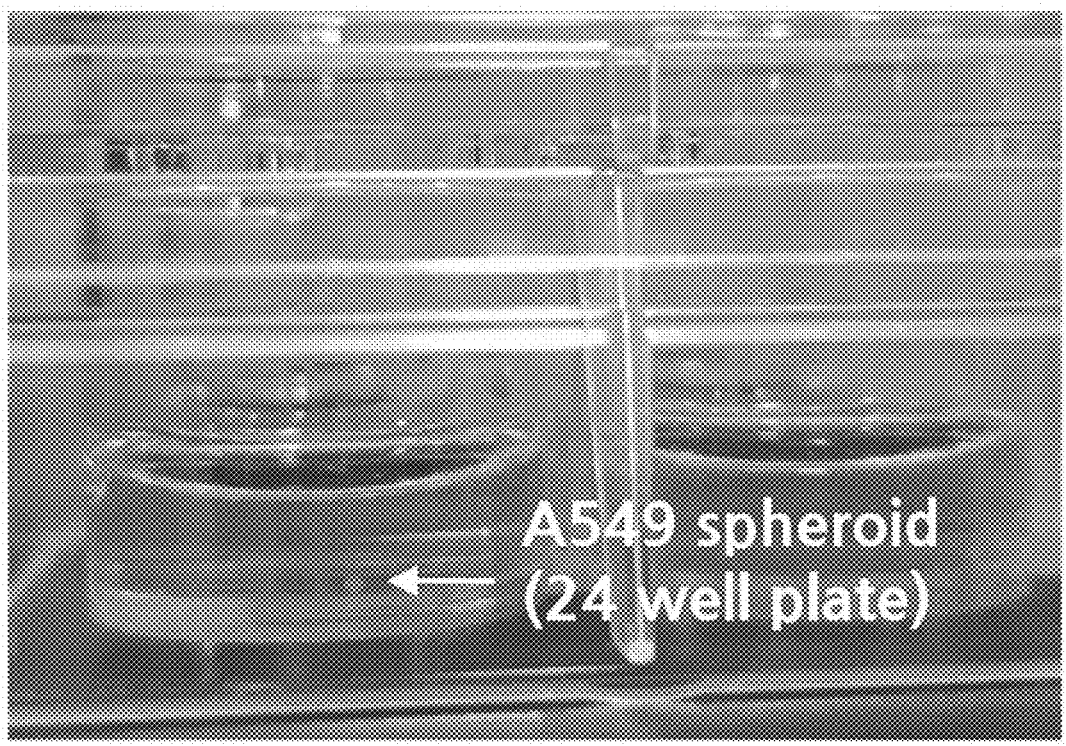

[Figure 3]
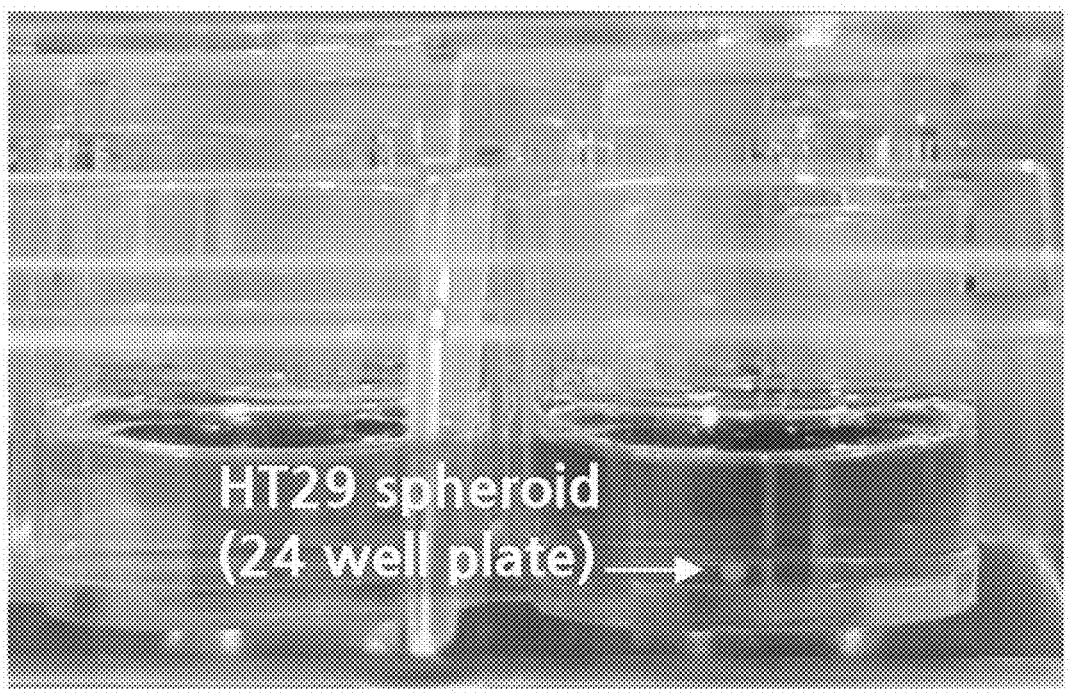

[Figure 4]
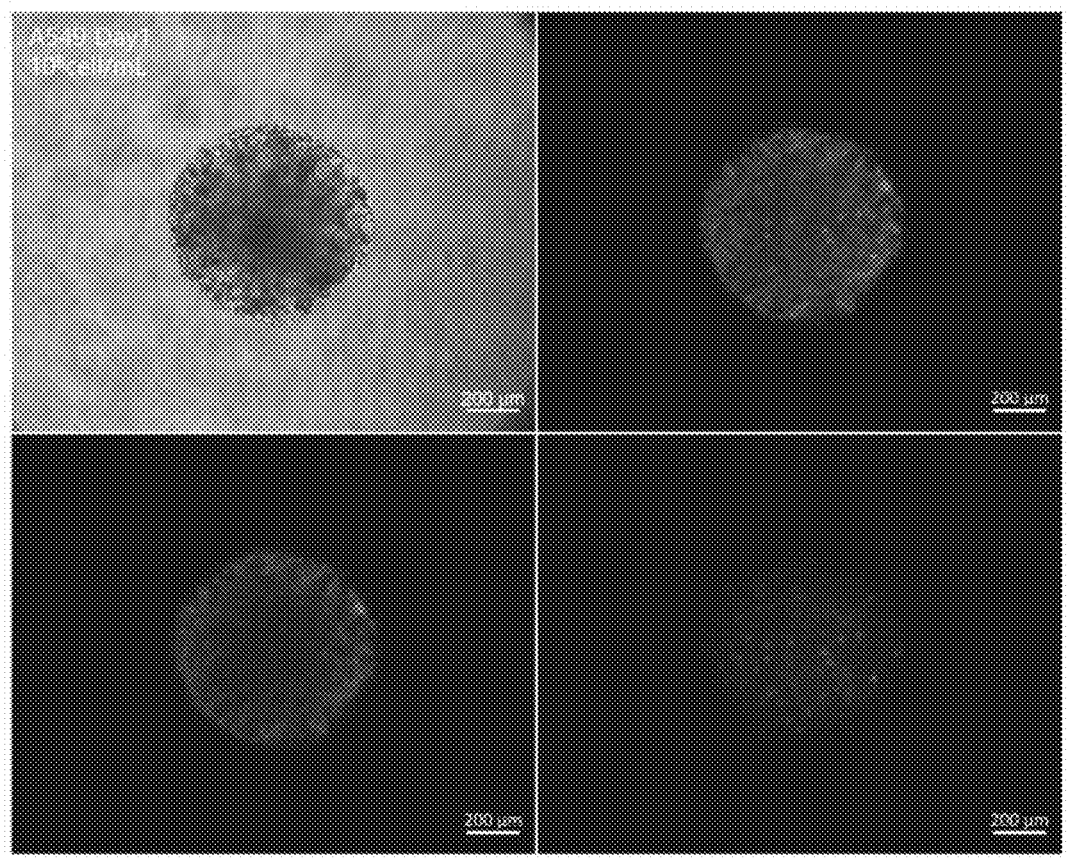

[Figure 5]
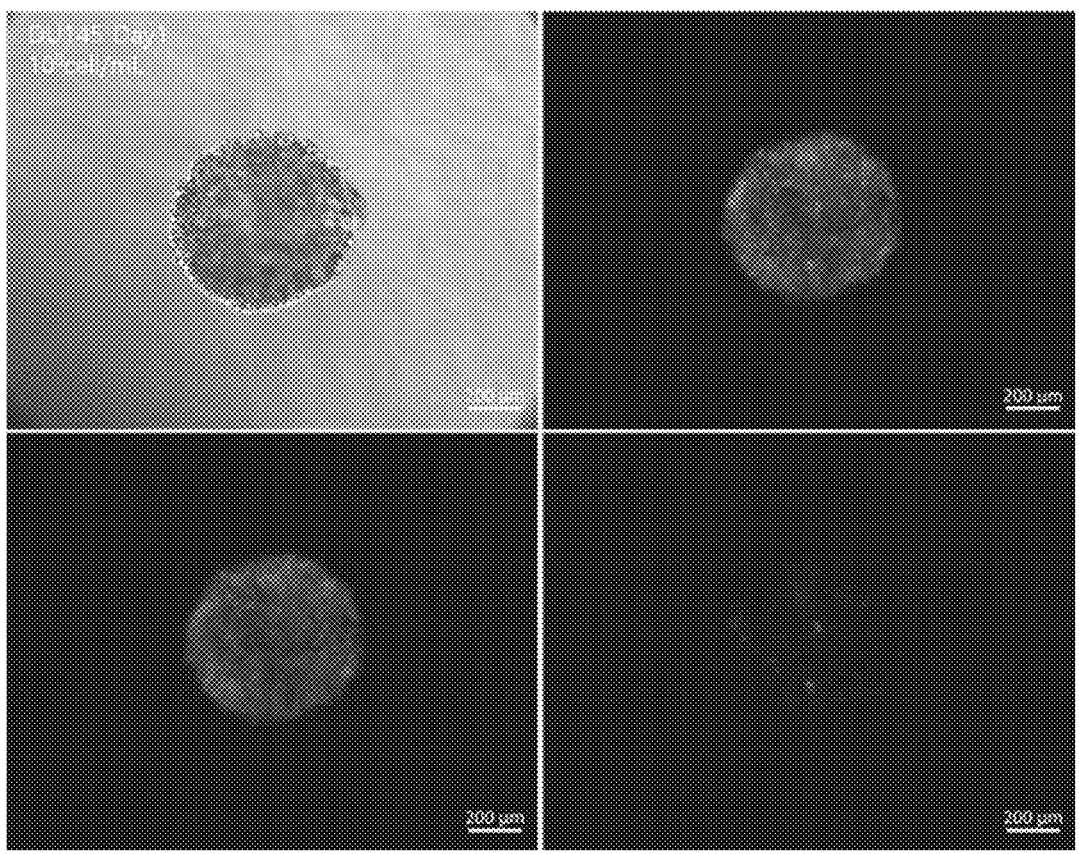

[Figure 6]
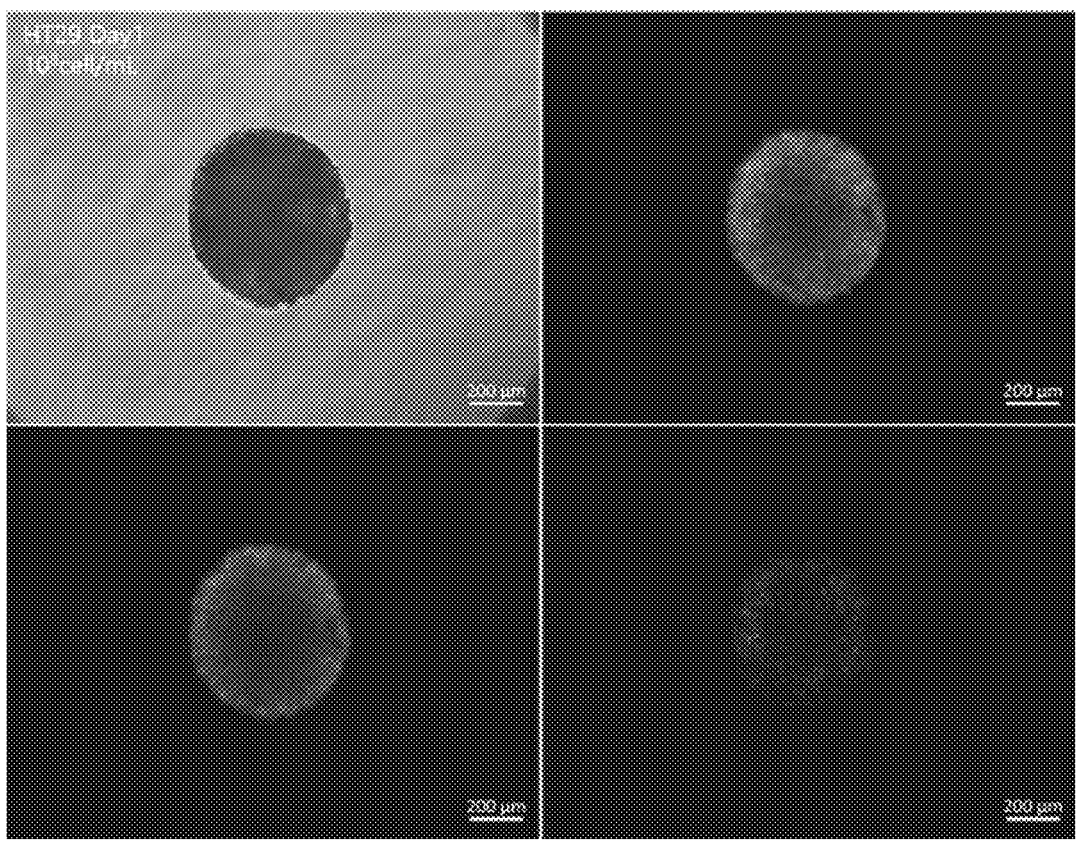

[Figure 7]
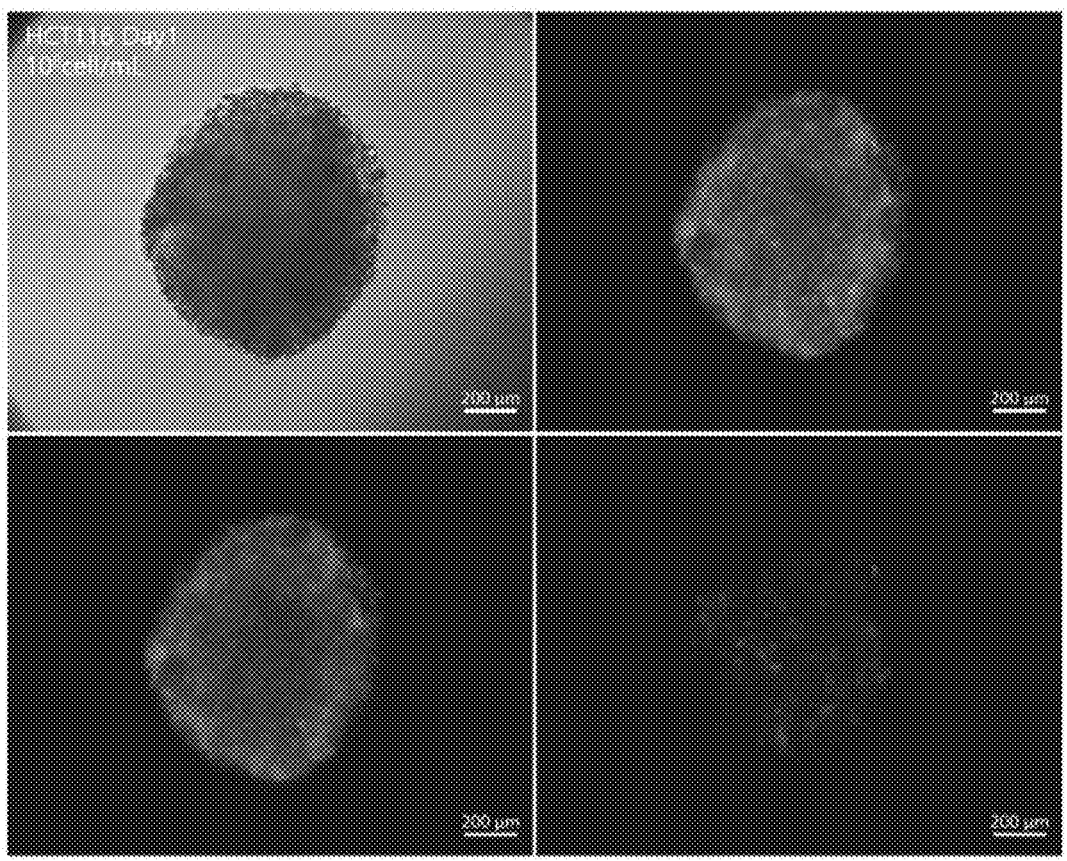

[Figure 8]
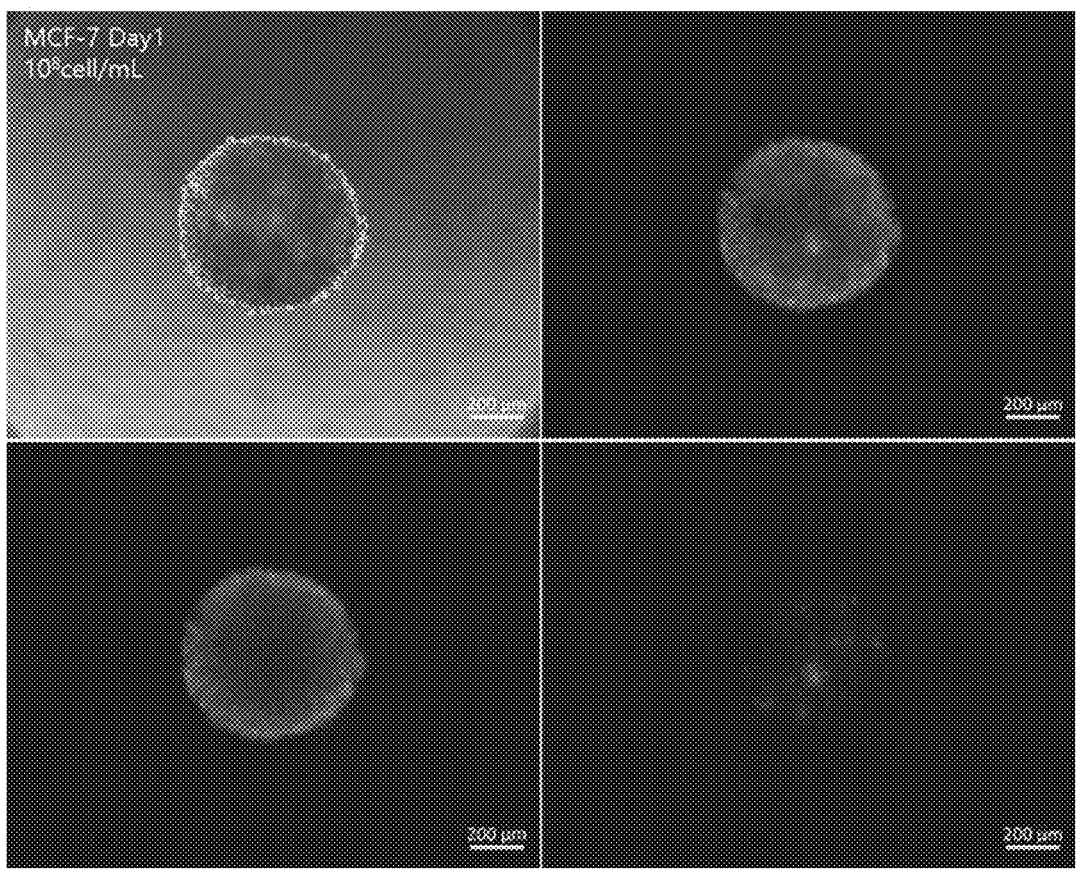

[Figure 9]
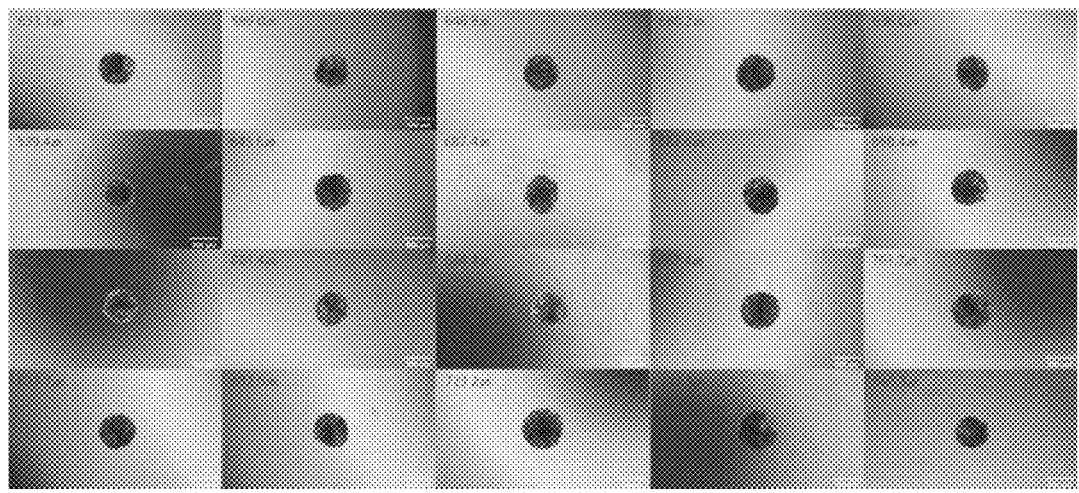

[Figure 10]
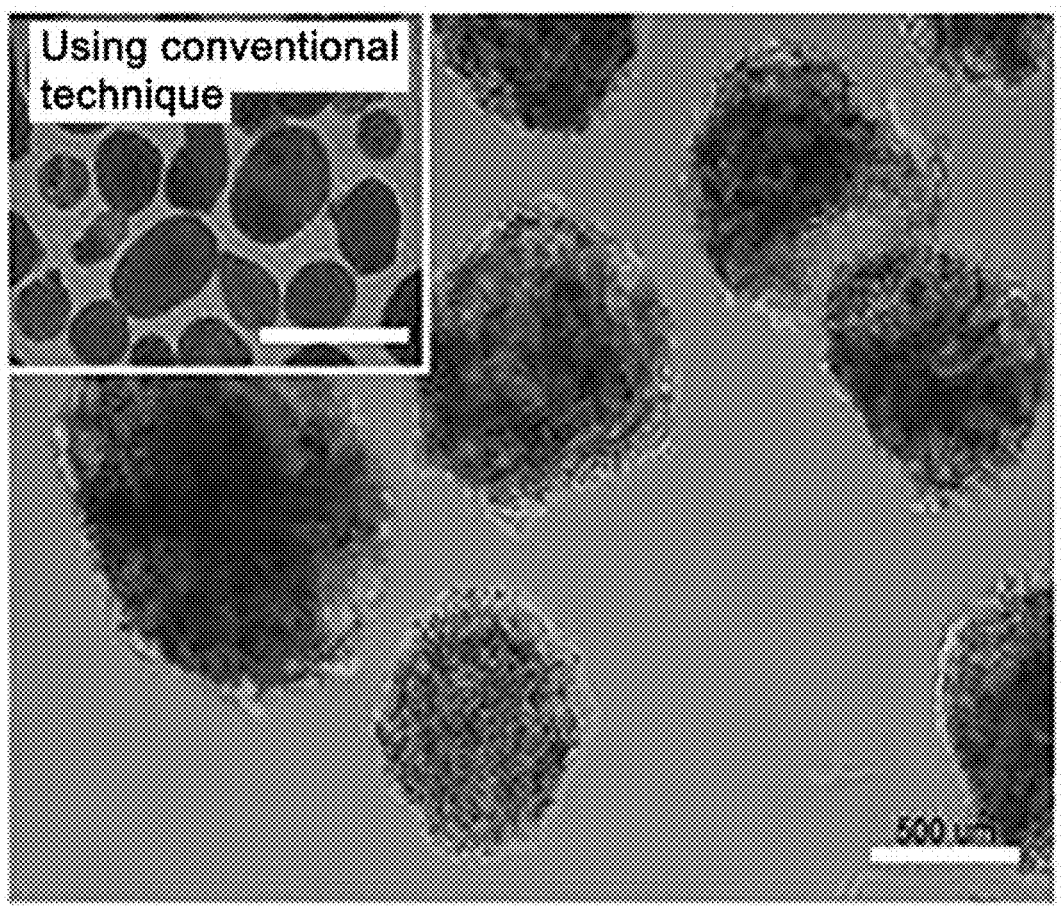

[Figure 11]
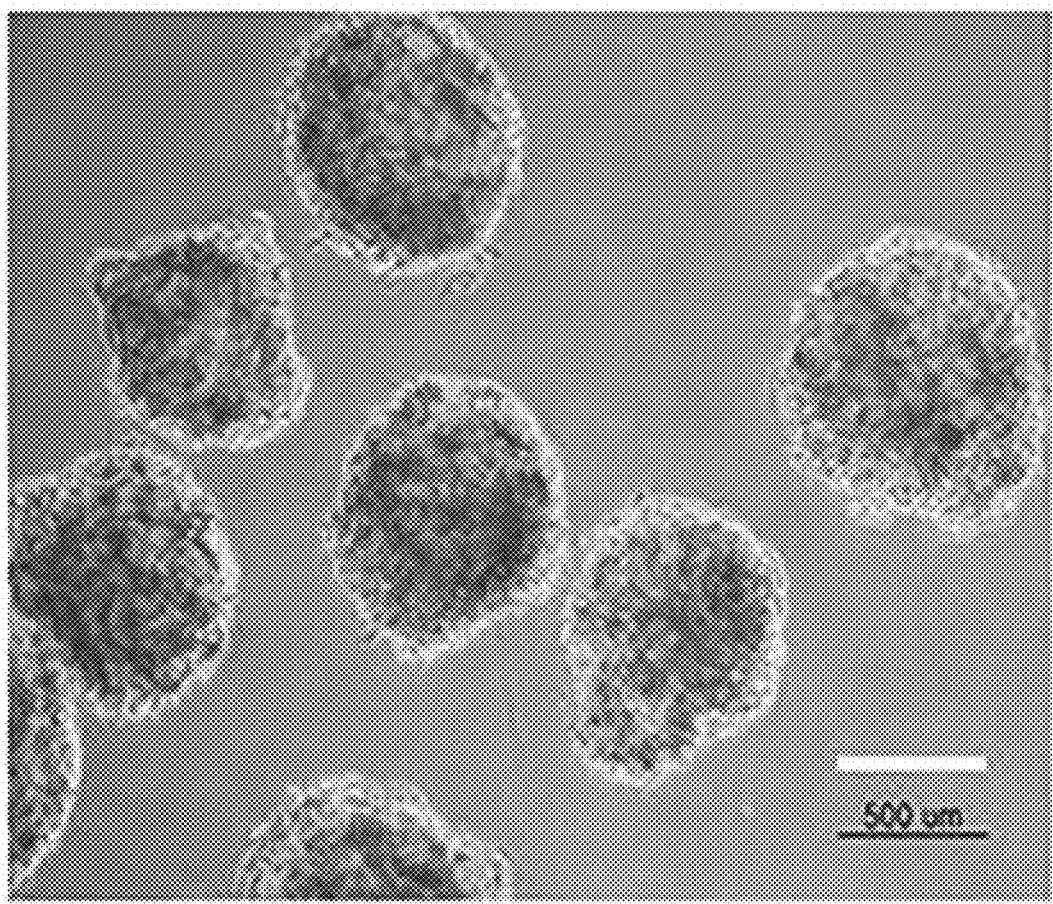

[Figure 12]
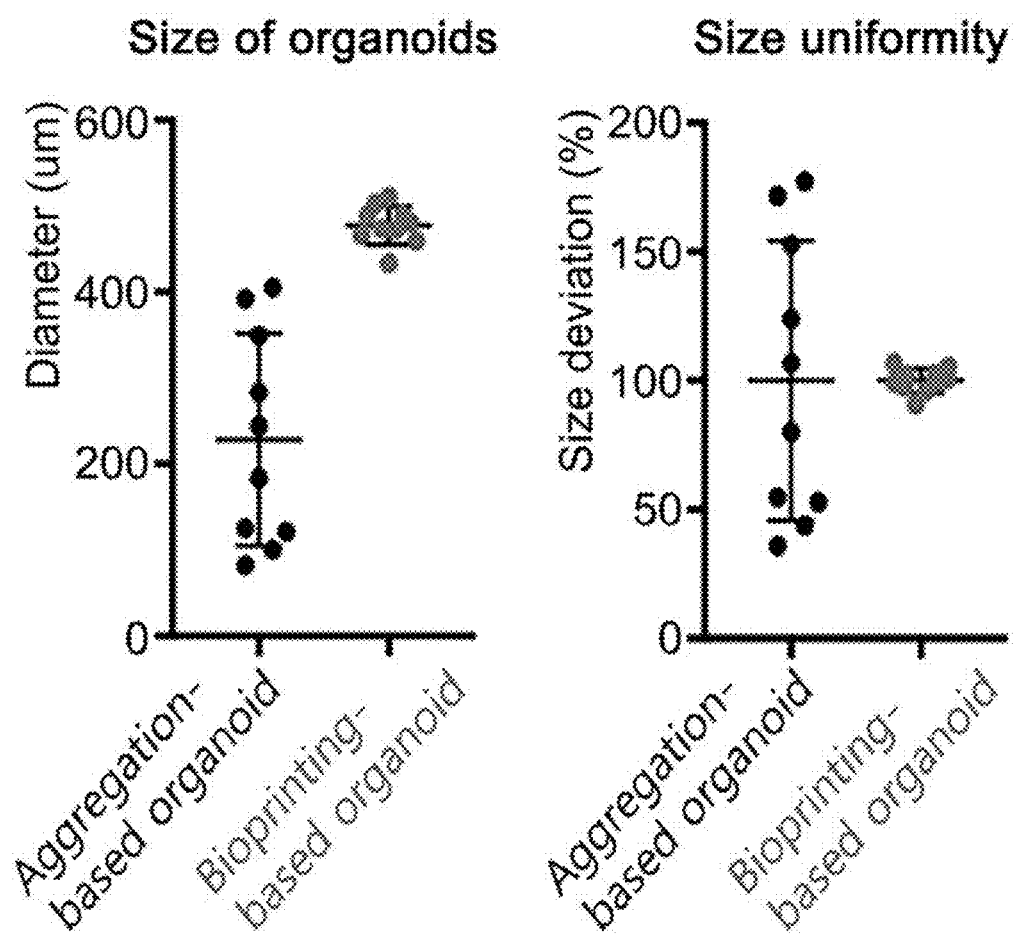

METHOD OF MANUFACTURING SPHEROID HAVING UNIFORM SIZE

CROSS REFERENCE TO RELATED APPLICATION

The present application claims priority based on Korean Patent Application No. 10-2019-0174204, filed on Dec. 24, 2019, the entire content of which is incorporated herein for all purposes by this reference.

BACKGROUND OF THE INVENTION

1. Technical Field

The present invention relates to a method of manufacturing a spheroid, and more particularly to a method of manufacturing a spheroid using a composition for a liquid bath for dipping a hydrogel droplet and a spheroid manufactured thereby.

2. Description of the Related Art

Recently, organs and tissue transplants are becoming more common worldwide in order to regenerate or replace damaged organs or tissues in human bodies. However, the shortage of donors for organ transplants is becoming more severe, and thus research is ongoing to develop artificial tissues and organs. For example, in order to develop artificial tissues and organs, methods of manufacturing complete artificial tissues and organs by injecting cells retaining the potential to develop into the tissues and organs to be manufactured into a 3D scaffold and providing a culture environment suitable for the injected cells have been used. Moreover, 3D bioprinting technology for outputting bioink containing cells is receiving attention.

3D bioprinting is technology for printing living cells with bioink to create artificial 3D structures or scaffolds that may be implanted into human bodies, and thorough research that may help to cure diseases, such as organoids, organs-on-chips, tissue and organ analogs for replacing the use of animal, etc., using 3D bioprinting techniques is ongoing.

Recently, actual in-vivo cell responses have been implemented with more detailed modeling using advanced 3D cell culture methods such as those pertaining to tumor spheroids, stem cell organoids, and tissue engineering through 3D bioprinting. In this process, attempts to realize 3D bioprinting systems having various structures have been made, and detailed problems that occur in the process of cell culture have emerged.

Specifically, the spheroid made by the existing aggregation method has a problem of low uniformity, and the hanging-drop method enables the formation of a uniform spheroid, but is problematic in that errors are likely to occur depending on the researcher due to the high difficulty of processing.

CITATION LIST

Patent Literature (Patent Document 1) Korean Patent Application Publication No. 10-2018-0117179 (Oct. 26, 2018)

SUMMARY OF THE INVENTION

The present inventors have studied techniques for rapidly manufacturing uniform spheroids and have ascertained that a spheroid, which is a 3D spherical structure that is difficult to implement on a planar substrate, may be formed using a liquid bath, thereby reproducibly manufacturing a 3D spherical structure by placing the bath composition in an existing container used by users, rather than a special container.

Accordingly, an objective of the present invention is to provide a method of manufacturing a spheroid, in which a spheroid, which is a 3D spherical structure that is difficult to implement on a planar substrate, may be formed in a uniform size, and a spheroid manufactured thereby.

An aspect of the present invention provides a method of manufacturing a spheroid, including (a) preparing a hydrogel and a composition for a liquid bath for dipping a droplet, (b) forming a hydrogel droplet by discharging the hydrogel from the nozzle of a hydrogel discharge device, (c) dipping the formed hydrogel droplet in the composition for a liquid bath for dipping a droplet, and (d) separating the hydrogel droplet by moving the nozzle of the hydrogel discharge device from the liquid surface of the composition for a liquid bath for dipping a droplet.

In an embodiment of the present invention, the hydrogel in step (a) may include any one selected from the group consisting of a cell, a drug and mixtures thereof.

In an embodiment of the present invention, the cell in step (a) may be any one selected from the group consisting of a lung cancer cell, colorectal cancer cell, prostate cancer cell, breast cancer cell, gastric cancer cell, liver cancer cell, brain cancer cell, kidney cancer cell, embryonic stem cell, adult stem cell, mesenchymal stem cell, induced pluripotent stem cell, adipose-derived stem cell, fibroblast, muscle cell, osteoblast, chondrocyte, adipocyte, hepatocyte, kidney cell, vascular endothelial cell, nerve cell, immune cell and mixtures thereof.

In an embodiment of the present invention, the hydrogel in step (a) may include an extracellular matrix material or an extracellular matrix-like material. Here, the extracellular matrix-like material may be any one selected from the group consisting of gelatin, collagen, alginate, chitosan, hyaluronic acid, dextran, fibrin, fibroin, Matrigel and mixtures thereof, and the extracellular matrix material or the extracellular matrix-like material may be independently used in an amount of 0.1 to 20 wt % based on the total weight of the hydrogel.

In an embodiment of the present invention, the composition for a liquid bath for dipping a droplet in step (a) may include a surfactant and a thickener, and may further include a curing agent. Here, the curing agent may be any one selected from the group consisting of transglutaminase, genipin, glutaraldehyde, diisocyanate, carbodiimide, calcium chloride, thrombin and mixtures thereof, and may be used in an amount of 1 to 10 wt % based on the total weight of the composition for a liquid bath for dipping a droplet.

In an embodiment of the present invention, step (d) may further include curing the hydrogel droplet after separating the hydrogel droplet.

Another aspect of the present invention provides a spheroid manufactured by the above method.

In a method of manufacturing a spheroid using a composition for a liquid bath for dipping a hydrogel droplet according to the present invention, the composition for a liquid bath for dipping a hydrogel droplet enables a droplet discharged from the nozzle of a hydrogel discharge device to float in the bath composition while maintaining the spherical shape of a spheroid and also minimizing the impact at the time of separation from the nozzle, thereby making it possible to quickly and uniformly manufacture spheroids compared to conventional methods of manufacturing spheroids such as aggregation methods or hanging-drop methods using bioreactors or low-attachment plates. Moreover, the present invention can be utilized in an automated manner regardless of the researcher's technical expertise, and thus can be applied to high-throughput screening (HTS) analysis. Furthermore, it has been found that a spheroid having a 3D spherical shape that is difficult to implement on a planar substrate can be successfully formed.

Therefore, the method of manufacturing a spheroid using a composition for a liquid bath for dipping a hydrogel droplet according to the present invention can be efficiently used in a technique for obtaining a spheroid having a 3D spherical shape and a uniform size in the field of spheroid production, such as the field of 3D cell culture, etc.

BRIEF DESCRIPTION OF DRAWINGS

FIG. 1 schematically shows a process of manufacturing a spheroid;

FIG. 2 is a photograph showing an A549 (lung cancer cell line) spheroid cultured on a culture plate;

FIG. 3 is a photograph showing an HT29 (colorectal cancer cell line) spheroid cultured on a culture plate;

FIG. 4 is images showing the A549 [lung cancer cell line] spheroid using a fluorescent microscope [top left: bright field image; top right: merged fluorescence image; bottom left: calcein AM (green fluorescence) image, live cells; bottom right: ethidium homodimer-1 (red fluorescence) image, dead cells];

FIG. 5 is images showing the DU145 (prostate cancer cell line) spheroid [top left: bright field image; top right: merged fluorescence image; bottom left: calcein AM (green fluorescence) image, live cells; bottom right: ethidium homodimer-1 (red fluorescence) image, dead cells];

FIG. 6 is images showing the HT29 (colorectal cancer cell line) spheroid [top left: bright field image; top right: merged fluorescence image; bottom left: calcein AM (green fluorescence) image, live cells; bottom right: ethidium homodimer-1 (red fluorescence) image, dead cells];

FIG. 7 is images showing the HCT116 (colorectal cancer cell line) spheroid [top left: bright field image; top right: merged fluorescence image; bottom left: calcein AM (green fluorescence) image, live cells; bottom right: ethidium homodimer-1 (red fluorescence) image, dead cells];

FIG. 8 is images showing the MCF-7 (breast cancer cell line) spheroid [top left: bright field image; top right: merged fluorescence image; bottom left: calcein AM (green fluorescence) image, live cells; bottom right: ethidium homodimer-1 (red fluorescence) image, dead cells];

FIG. 9 is images showing A549 spheroids having various sizes manufactured using a 3D bioprinter;

FIG. 10 shows the first-day image of an organoid manufactured using a 3D bioprinter (the inset shows an organoid formed by a conventional technique);

FIG. 11 shows the seventh-day image of the organoid manufactured using a 3D bioprinter; and FIG. 12 is graphs showing the size of organoids and the size uniformity distribution of an aggregation-based organoid and a bioprinting-based organoid.

DESCRIPTION OF SPECIFIC EMBODIMENTS

As used herein, the term "droplet" refers to any binding volume of a hydrogel material (which may be a liquid or gel). The volume of a water droplet is generally less than 1.0 ml, but a viscous material may have a greater volume, and a minimum self-contained volume of a medium is referred to as a droplet.

As used herein, the term "spheroid" refers to a 3D structure formed such that cells are aggregated so that the cross section thereof is generally circular or elliptical.

The present invention pertains to a method of manufacturing a spheroid, including (a) preparing a hydrogel and a composition for a liquid bath for dipping a droplet, (b) forming a hydrogel droplet by discharging the hydrogel from the nozzle of a hydrogel discharge device, (c) dipping the formed hydrogel droplet in the composition for a liquid bath for dipping a droplet, and (d) separating the hydrogel droplet by moving the nozzle of the hydrogel discharge device from the liquid surface of the composition for a liquid bath for dipping a droplet.

The method of the present invention includes preparing a hydrogel and a composition for a liquid bath for dipping a droplet [step (a)]. In order to manufacture a spheroid using a hydrogel, in step (a), the hydrogel is prepared by mixing a hydrogel composition with an appropriate amount of a cell or drug, and the composition for a liquid bath for dipping a droplet able to accommodate the formed hydrogel droplet is prepared. In step (a), the hydrogel may include any one selected from the group consisting of a cell, a drug and mixtures thereof. The cell may be used without limitation so long as it is viable in a system for manufacturing a spheroid using the hydrogel discharge device, and may be any one selected from the group consisting of a lung cancer cell, colorectal cancer cell, prostate cancer cell, breast cancer cell, gastric cancer cell, liver cancer cell, brain cancer cell, kidney cancer cell, embryonic stem cell, adult stem cell, mesenchymal stem cell, induced pluripotent stem cell, adipose-derived stem cell, fibroblast, muscle cell, osteoblast, chondrocyte, adipocyte, hepatocyte, kidney cell, vascular endothelial cell, nerve cell, immune cell and mixtures thereof.

In an embodiment of the present invention, the hydrogel in step (a) may include an extracellular matrix material or an extracellular matrix-like material, in addition to the cell. The extracellular matrix-like material may be any one selected from the group consisting of gelatin, collagen, alginate, chitosan, hyaluronic acid, dextran, fibrin, fibroin, Matrigel and mixtures thereof. The extracellular matrix material or the extracellular matrix-like material is independently used in an amount of 0.1 to 20 wt %, and preferably 1 to 10 wt %, based on the total weight of the hydrogel.

Also, the hydrogel may include a thickener as necessary. The thickener may be any one selected from the group consisting of gellan gum, carrageenan gum, locust bean gum, xanthan gum, methyl cellulose, hydroxyethyl cellulose, hydroxypropyl starch phosphate, poloxamer and mixtures thereof. The thickener is used in an amount of 0.01 to 10 wt %, and preferably 0.1 to 1 wt %, based on the total weight of the hydrogel.

Also, the hydrogel may include a material that is cured by a curing agent, as necessary. Specifically, when the hydrogel droplet is discharged, dipped in the composition for a liquid bath for dipping a droplet and cured by the curing agent contained in the composition for a liquid bath, the material that is cured by the curing agent contained in the composition for a liquid bath for dipping a droplet may be included in the hydrogel composition.

In an embodiment of the present invention, the composition for a liquid bath for dipping a droplet in step (a) may include a surfactant and a thickener, and may further include a curing agent, as necessary.

In order to obtain a 3D spherical cell structure, which is a spheroid close to a sphere and is difficult to implement on a planar substrate, the composition for a liquid bath is capable of forming a spheroid, which is a spherical cell structure, by accommodating a droplet discharged from the nozzle of a hydrogel discharge device using a liquid bath.

In the present invention, the surfactant included in the composition for a liquid bath may be any one selected from the group consisting of polyoxyethylene-polyoxypropylene copolymer, sorbitan ester, polyoxyethylene sorbitan, polyoxyethylene ether and mixtures thereof. Specifically, the surfactant includes polyoxyethylene-polyoxypropylene copolymer [e.g. Poloxamer, Pluronic® F-127], sorbitan ester [e.g. Span™], polyoxyethylene sorbitan [e.g. Tween™], polyoxyethylene ether [e.g. Brij™] and the like.

In an embodiment of the present invention, the surfactant is used in an amount of 1 to 10 wt %, preferably 2 to 8 wt %, and more preferably 4 to 6 wt % based on the total weight of the composition.

In the present invention, the thickener included in the composition for a liquid bath serves to adjust the viscosity of the bath composition to an appropriate range so that the droplet discharged from the nozzle of the hydrogel discharge device floats in the bath composition while maintaining the spherical shape of a spheroid and minimizing the impact at the time of separation from the nozzle.

In the present invention, the thickener suitable for use in the composition for a liquid bath may be any one selected from the group consisting of gellan gum, carrageenan gum, locust bean gum, xanthan gum, methyl cellulose, hydroxyethyl cellulose, hydroxypropyl starch phosphate, poloxamer and mixtures thereof.

In an embodiment of the present invention, the thickener is used in an amount of 0.001 to 10 wt %, preferably 0.005 to 5 wt %, and more preferably 0.01 to 1 wt %, based on the total weight of the composition.

In the method of the present invention, the curing process, which is performed during the dipping process in step (c) and the hydrogel droplet separation process in step (d), may be performed with or without the use of a curing agent. When using a curing agent, the composition for a liquid bath may include a curing agent. Here, the curing agent functions to cure the hydrogel droplet discharged from the nozzle of the hydrogel discharge device. On the other hand, when the hydrogel droplet is cured without the use of a curing agent, the composition for a liquid bath includes no curing agent, and for example, collagen included in the hydrogel may be cured at a temperature adjusted to 37° C. or more, or gellan gum may be cured using cations at a temperature of 37° C. or more.

As the curing agent, any material may be used without limitation, so long as it is able to cure the hydrogel droplet by curing the material contained in the hydrogel droplet, and the curing agent may be any one selected from the group consisting of a gelatin curing agent, such as transglutaminase (gelatin curing agent), genipin, glutaraldehyde, diisocyanate and carbodiimide, an alginate curing agent, such as calcium chloride, a fibrinogen curing agent, such as thrombin, and mixtures thereof.

In an embodiment of the present invention, the curing agent is used in an amount of 1 to 10 wt %, and preferably 2 to 5 wt %, based on the total weight of the composition.

In an embodiment of the present invention, the composition for a liquid bath for dipping a hydrogel droplet preferably includes poloxamer (polyoxyethylene-polyoxypropylene copolymer), gellan gum and transglutaminase, and most preferably includes, based on the total weight of the composition, 1 to 10 wt % of poloxamer (polyoxyethylene-polyoxypropylene copolymer), 0.001 to 10 wt % of gellan gum and 1 to 10 wt % of transglutaminase.

The method of the present invention includes forming a hydrogel droplet by discharging the hydrogel from the nozzle of a hydrogel discharge device [step (b)]. In step (b), the hydrogel discharge device may be used without limitation, so long as it is able to adjust and/or determine the position of the nozzle from which the hydrogel is discharged, and examples thereof may include, but are not limited to, a bioprinting device and the like. By appropriately adjusting discharge conditions such as the nozzle diameter of the hydrogel discharge device, the discharge time, and the pressure, the size of the hydrogel droplet may be controlled, and is optimized depending on the specification of the discharge device that is used. Preferably, the hydrogel droplet is formed to a size of 2 mm or less, and more preferably 1 mm or less.

The method of the present invention includes dipping the formed hydrogel droplet in the composition for a liquid bath for dipping a droplet [step (c)]. Step (c) is moving the nozzle in which the hydrogel droplet is formed downwards to the liquid surface of a liquid bath so that the hydrogel droplet enters the liquid bath (dipping gelation step). This step is carried out based on the principle whereby the formed hydrogel droplet is separated from the nozzle due to a change in surface tension attributable to dipping, and since the spherical shape of the droplet spheroid is deformed when the tip of the nozzle enters the water to a depth greater than the size of the hydrogel droplet, it is necessary to optimize the position of the nozzle depending on the size of the droplet to be manufactured. This step is based on the principle whereby the hydrogel droplet is separated due to the change in surface tension attributable to dipping. As such, the combination of the liquid bath and the hydrogel is important in order to separate the droplet formed outside the bath while maintaining the shape of the droplet.

The method of the present invention includes separating the hydrogel droplet by moving the nozzle of the hydrogel discharge device from the liquid surface of the composition for a liquid bath for dipping a droplet [step (d)]. Step (d) is performed immediately after step (c), and the output nozzle of the hydrogel discharge device is moved to the origin, whereby the nozzle and the droplet are separated from each other.

During the dipping process in step (c) and the hydrogel droplet separation process in step (d), the hydrogel droplet is cured, and thus a spheroid having a spherical shape is formed. Here, the curing process may be performed with or without the use of a curing agent. In addition to the curing during the dipping process in step (c) and the hydrogel droplet separation process in step (d), step (d) may further include curing the formed spheroid, as necessary, after separation of the hydrogel droplet. As such, the curing reaction using a curing agent may be additionally carried out, or a curing process using a predetermined temperature may be performed. During the curing process using a predetermined temperature, the temperature is set to the range of 30 to 38° C., and preferably 35 to 37° C., and the curing time may vary depending on the properties of the hydrogel that is used.

In addition, the present invention pertains to a spheroid manufactured by the above method. The spheroid manufactured by the above method is obtained in a uniform size compared to a conventional aggregation-based organoid, and the organoid obtained after culture is maintained in a uniform size compared to the aggregation-based organoid.

A better understanding of the present invention will be given through the following examples. However, these examples are merely set forth to illustrate the present invention, and are not to be construed as limiting the scope of the present invention.

Examples

1. Spheroid Production
(1) Summary

In order to form a 3D spherical cell structure, which is difficult to implement on a planar substrate, using a liquid bath, the following method was performed. As the container used herein, any container may be used, so long as the bath is capable of being placed in an existing container used by users, rather than a special container, and the present technique may be implemented together with any device capable of introducing a bioink droplet to the water-surface position of the bath in an adjustable manner.

(2) Technical Content

The composition for a liquid bath is shown in Table 1 below and the bioink composition is shown in Table 2 below.

TABLE 1

| Material | Mixing ratio | Function |
|---|---|---|
| Pluronic F-127 | 5% | Thickener/surfactant |
| Gellan gum | 0.03-0.33% | Thickener |
| Transglutaminase | 3% | Curing agent (gelatin) |

TABLE 2

| Material | Mixing ratio* | Function |
|---|---|---|
| Gelatin | 6-7.5% | Extracellular matrix (ECM) |
| Gellan gum | 0.45-0.67% | Thickener |

Pluronic F-127 was used for mixing in the form of a 15% Pluronic F-127 solution in Dulbecco's phosphate-buffered saline (DPBS), and transglutaminase was used for mixing in the form of a 10 transglutaminase solution in Dulbecco's phosphate-buffered saline (DPBS).

Gellan gum was used at the above mixing ratio in the form of a 1% gellan gum solution in deionized water.

Transglutaminase, used as the curing agent, was contained in the composition for a liquid bath in order to cure the gelatin component of the bioink, and may be removed from the composition or replaced with another curing material depending on the properties of the bioink output into the liquid bath.

The composition for a liquid bath may be prepared using the thickener in an amount that varies depending on the viscosity of the bioink that is used. The combination of liquid bath and bioink is important in the formation of a spherical shape.

2. Method of Manufacturing Spheroid
(1) Summary

It is difficult to uniformly manufacture a 3D spherical cell structure on a planar substrate, and this problem is intended to be solved with a liquid bath and a bioink discharge device. By this method, a repeatedly reproducible 3D spherical cell structure may be manufactured, the size of the spherical shape may be adjusted depending on the diameter of the nozzle, and the viscous material, which is difficult to use with a micropipette, may be uniformly discharged using bioprinting.

(2) Technical Content

The manufacturing method is summarized in FIG. 1 and the manufacturing sequence is as follows.

① An liquid bath was placed in a container, and bioink (hydrogel) mixed with cells was placed in an barrel, which was then mounted to a printer.

② The bioink was discharged to the size of a spheroid for the manufacture thereof, thus forming a droplet (beading step). Here, the size of the droplet may be adjusted depending on the discharge conditions, such as the nozzle diameter, discharge time, pressure, etc., and is optimized depending on the specifications of the discharge device that is used.

③ The nozzle at the end of which the bioink droplet forms was moved downwards to the liquid surface of the bath to cause the droplet to enter the bath (dipping gelation step). The formed bioink droplet was separated from the nozzle due to the change in the surface tension attributable to dipping. Since the spherical shape is deformed when the tip of the nozzle enters the bath to a depth greater than the size of the bioink droplet, it is necessary to optimize the position of the nozzle depending on the size of the spheroid to be manufactured. This step is based on the principle whereby the bioink droplet is separated due to the change in surface tension attributable to dipping. As such, the combination of the liquid bath and the bioink is important in order to separate the droplet formed outside the bath while maintaining the shape of the droplet.

④ The droplet was separated from the nozzle by moving the nozzle to the origin.

⑤ As needed, curing was carried out at 37° C. for 30 min. Here, the curing conditions may vary depending on the properties of the bioink that is used.

3. Manufacture of Spheroid

A cancer spheroid was manufactured using a 3D bioprinter as follows.

① A cell pellet for spheroid output ($10^8$ cells) was suspended in 1 ml of bioink (0.67% gellan gum+6% gelatin in DPBS) preheated to 37° C. and loaded into the output barrel of a 3D bioprinter. A liquid bath (0.1% gellan gum, 5% Pluronic F-127, 3% transglutaminase in DPBS) was placed in an amount of 400 μl/well into a 24-well plate.

② A bioink droplet was output into the 24-well plate filled with the liquid bath at a pressure of 20 kPa using a 30 G (blunt-tipped) nozzle.

③ Curing was performed for 30 min in an incubator (37° C.).

④ After removal of the liquid bath and washing with 1 ml of DPBS, the resulting spheroid was cultured in a low-attachment well plate.

Culture medium: RPMI+10% FBS+1% antibiotic antimycotic solution, 1 ml/well

Culture conditions: 37° C., 5% $CO_2$

Photographs of the culture plate containing the spheroid therein are shown in FIG. 2 (A549, lung cancer cell line) and in FIG. 3 (HT29, colorectal cancer cell line).

4. Live/Dead Assay of Cancer Cell Spheroid Manufactured Using 3D Bioprinter

① A cell pellet for spheroid output ($10^8$ cells) was suspended in 1 ml of bioink (0.67% gellan gum+6% gelatin in DPBS) preheated to 37° C. and loaded into the output barrel of a 3D bioprinter. A liquid bath was placed in an amount of 400 μl/well into a 24-well plate.

② A bioink droplet was output into the 24-well plate filled with the liquid bath at a pressure of 20 kPa using a 30 G (blunt-tipped) nozzle.

③ Curing was performed at 37° C. for 30 min.

④ After removal of the liquid bath and washing with 1 ml of DPBS, the resulting spheroid was cultured in a low-attachment well plate. Culturing was carried out in a culture medium (RPMI+10% FBS+1% antibiotic antimycotic solution) at 1 ml/well for 24 hr (37° C., 5% $CO_2$).

⑤ After removal of the culture medium and washing two times with 1 ml/well of DPBS, treatment with a fluorescent reagent (a DPBS solution including 4 μM ethidium homodimer-1 and 1 μM calcein AM) was performed.

⑥ After reaction at room temperature for 30 min, observation was performed using a fluorescent microscope (Ex/Em: calcein=494/517 nm, ethidium homodimer-1 528/617 nm).

Images of the A549 (lung cancer cell line) spheroid are shown in FIG. 4.

Images of the DU145 (prostate cancer cell line) spheroid are shown in FIG. 5.

Images of the HT29 (colorectal cancer cell line) spheroid are shown in FIG. 6.

Images of the HCT116 (colorectal cancer cell line) spheroid are shown in FIG. 7.

Images of the MCF-7 (breast cancer cell line) spheroid are shown in FIG. 8.

5. Analysis of Size Distribution of A549 Spheroid Manufactured Using 3D Bioprinter
<Experimental Method>

① A cell pellet for spheroid output ($10^8$ cells) was suspended in 1 ml of bioink (0.67% gellan gum+6% gelatin in DPBS) preheated to 37° C. and loaded into the output barrel of a 3D bioprinter. A liquid bath was placed in an amount of 400 μl/well into a 24-well plate.

② A bioink droplet was output into the 24-well plate filled with the liquid bath at a pressure of 20 kPa using a 30 G (blunt-tipped) nozzle.

③ Curing was performed at 37° C. for 30 min.

④ After removal of the liquid bath and washing with 1 ml of DPBS, spheroid images were obtained using a microscope. The images thus obtained are shown in FIG. 9.

⑤ The diameter of the spheroid was measured using image J software, and the average diameter and standard deviation thereof were determined to be 645.78 μm and 49.46 μm, respectively.

6. Culture of Organoid Manufactured Using 3D Bioprinter and Size Uniformity Analysis ① A human embryonic stem cell (H9) pellet ($10^8$ cells) was suspended in 1 ml of bioink (0.67% gellan gum+6 gelatin in DPBS) preheated to 37° C. and loaded into the output barrel of a 3D bioprinter. A liquid bath was placed in an amount of 400 μl/well into a 24-well plate.

② A bioink droplet was output into the 24-well plate filled with the liquid bath at a pressure of 20 kPa using a 30 G (blunt-tipped) nozzle.

③ Curing was performed at 37° C. for 30 min.

④ After removal of the liquid bath and washing two times with 1 ml/well of DPBS, the resulting spheroid was cultured in a culture medium.

Culture medium: Essential 8 (Gibco)
Culture conditions: CERO (Bench-top incubator & Bioreactor), 37° C., 5% $CO_2$ FIG. 10 shows the first-day image of an organoid manufactured using a 3D bioprinter (the inset shows an organoid formed by a conventional technique), and FIG. 11 shows the seventh-day image of the organoid manufactured using a 3D bioprinter.

In addition, FIG. 12 is graphs showing the size of organoids and the size uniformity distribution of the aggregation-based organoid and the bioprinting-based organoid.

As shown in FIGS. 10, 11 and 12, the organoid size is more uniform for the bioprinting-based organoid than for the conventional aggregation-based organoid.

Although specific embodiments of the present invention have been disclosed in detail as described above, it will be obvious to those skilled in the art that such description is merely of preferable exemplary embodiments and is not to be construed to limit the scope of the present invention. Therefore, the substantial scope of the present invention will be defined by the appended claims and equivalents thereof.

What is claimed is:

1. A method of manufacturing a spheroid, comprising:
(a) preparing a hydrogel and a composition for a liquid bath for dipping a droplet;
(b) forming a hydrogel droplet by discharging the hydrogel from a nozzle of a hydrogel discharge device;
(c) dipping the formed hydrogel droplet in the composition by moving an end of the nozzle downward to a liquid surface of the composition; and
(d) separating the hydrogel droplet by moving the nozzle of the hydrogel discharge device from the liquid surface of the composition,
wherein in step (d), the hydrogel droplet is released at the surface of the composition while the nozzle does not go through the liquid surface,
wherein the composition in step (a) consists of a surfactant, a thickener, and optionally one or more of a curing agent, Dulbecco's phosphate-buffered saline, and water,
wherein the surfactant is any one selected from the group consisting of polyoxyethylene-polyoxypropylene copolymer, sorbitan ester, polyoxyethylene sorbitan, polyoxyethylene ether and mixtures thereof,
wherein the thickener is any one selected from the group consisting of gellan gum, carrageenan gum, locust bean gum, xanthan gum, methyl cellulose, hydroxyethyl cellulose, hydroxypropyl starch phosphate, poloxamer and mixtures thereof, and
wherein the curing agent is any one selected from the group consisting of transglutaminase, genipin, glutaraldehyde, diisocyanate, carbodiimide, calcium chloride, thrombin and mixtures thereof.

2. The method of claim 1, wherein the hydrogel in step (a) comprises any one selected from the group consisting of a cell, a drug and mixtures thereof.

3. The method of claim 2, wherein the cell in step (a) is any one selected from the group consisting of a lung cancer cell, colorectal cancer cell, prostate cancer cell, breast cancer cell, gastric cancer cell, liver cancer cell, brain cancer cell, kidney cancer cell, embryonic stem cell, adult stem cell, mesenchymal stem cell, induced pluripotent stem cell, adipose-derived stem cell, fibroblast, muscle cell, osteoblast, chondrocyte, adipocyte, hepatocyte, kidney cell, vascular endothelial cell, nerve cell, immune cell and mixtures thereof.

4. The method of claim 1, wherein the hydrogel in step (a) comprises an extracellular matrix material or an extracellular matrix-like material.

5. The method of claim 4, wherein the extracellular matrix-like material is any one selected from the group consisting of gelatin, collagen, alginate, chitosan, hyaluronic acid, dextran, fibrin, fibroin and mixtures thereof.

6. The method of claim 4, wherein the extracellular matrix material or the extracellular matrix-like material is independently used in an amount of 0.1 to 20 wt % based on a total weight of the hydrogel.

7. The method of claim 1, wherein the curing agent is used in an amount of 1 to 10 wt % based on a total weight of the composition for a liquid bath for dipping a droplet.

8. The method of claim 1, wherein step (d) further comprises curing the hydrogel droplet after separating the hydrogel droplet.

\* \* \* \* \*